United States Patent [19]

Swartz

[11] 4,305,390
[45] Dec. 15, 1981

[54] METHOD FOR GENERATING OXYGEN IN AN EXCITED ELECTRONIC STATE AND INACTIVATION OF MICROORGANISMS

[75] Inventor: Mitchell R. Swartz, Malden, Mass.

[73] Assignee: Massachusetts Institute of Technology, Cambridge, Mass.

[21] Appl. No.: 49,702

[22] Filed: Jun. 18, 1979

Related U.S. Application Data

[63] Continuation-in-part of Ser. No. 879,822, Feb. 21, 1978, Pat. No. 4,181,128, which is a continuation-in-part of Ser. No. 636,290, Nov. 28, 1975, Pat. No. 4,139,348.

[51] Int. Cl.³ .............................................. A61M 37/00
[52] U.S. Cl. ................................. 128/207.21; 128/362
[58] Field of Search ........................... 128/362, 207.21; 424/127, 90; 204/129, 155, 157.1 R, 157.1 HE, 176

[56] References Cited

U.S. PATENT DOCUMENTS

| | | | |
|---|---|---|---|
| 2,637,688 | 5/1953 | Ryan | 204/152.1 R |
| 3,019,168 | 1/1962 | Taylor | 424/90 |
| 3,456,053 | 7/1969 | Crawford | 424/90 |
| 3,557,783 | 1/1971 | Castner | 128/207.21 |
| 3,591,679 | 7/1971 | Voss | 424/127 |
| 4,181,128 | 1/1980 | Swartz | 128/207.21 |
| 4,199,419 | 4/1980 | Holroyd et al. | 204/157.1 R |

Primary Examiner—William E. Kamm
Attorney, Agent, or Firm—Arthur A. Smith, Jr.

[57] ABSTRACT

A system for inactivation of microorganisms and their products (viruses, bacteria, toxins and cells) such as, for example, Herpes simplex viruses by superposition of a component such as, for example, methylene blue (MB) plus light, oxygen and electricity. The system serves to generate the superoxide radical anion ($O_2^-$) and consequently hydrogen peroxide ($H_2O_2$) and the hydroxyl radical (OH.), both of which enter into the inactivation process, but each has use beyond said system. The disclosed activating components include methylene blue covalently bonded to conconavalin A to enhance its binding to mammalian lymphoblasts and compounds of d− and f− transition metals such as cis-platinum diamino dichloride.

4 Claims, 10 Drawing Figures

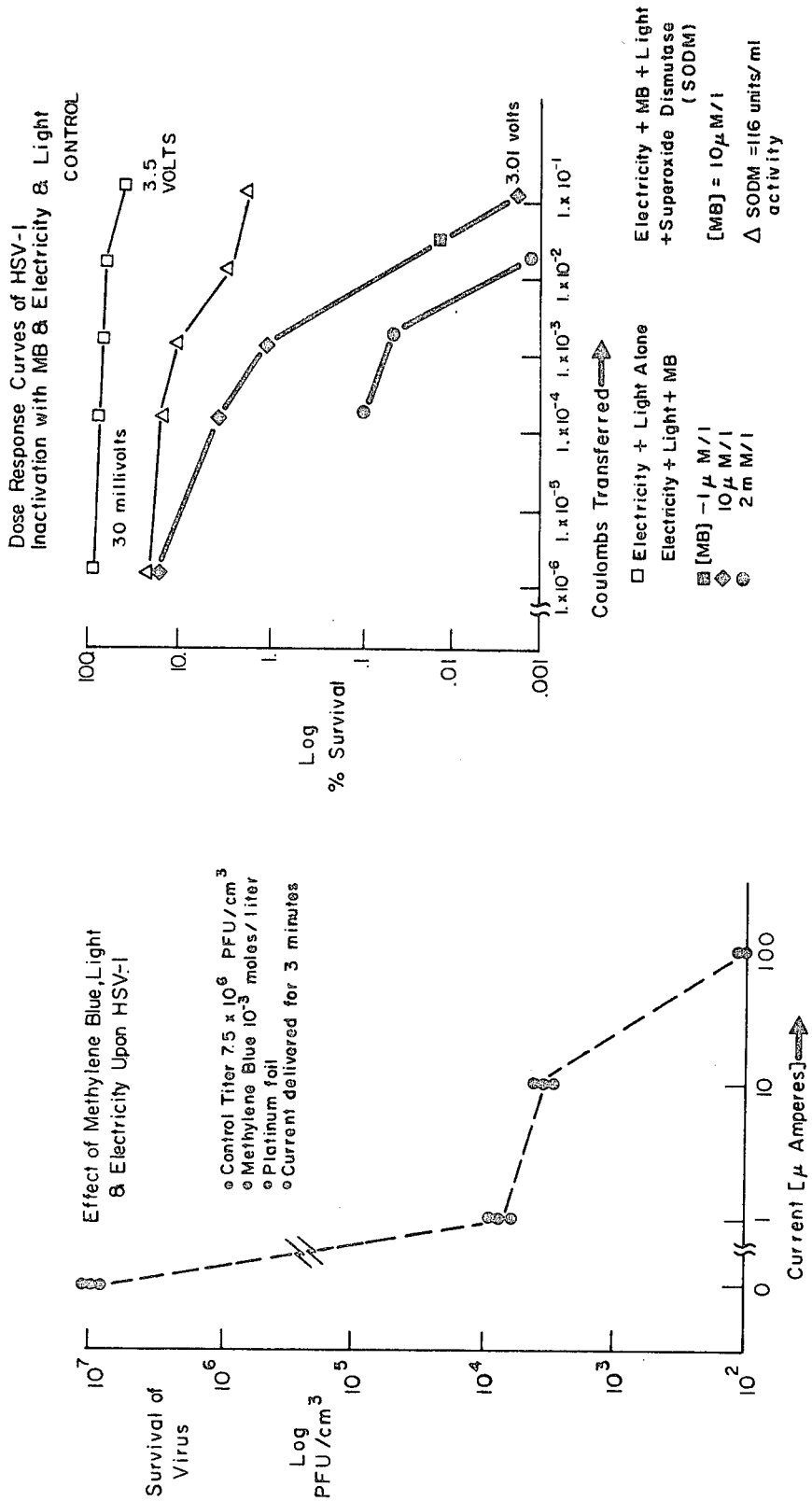

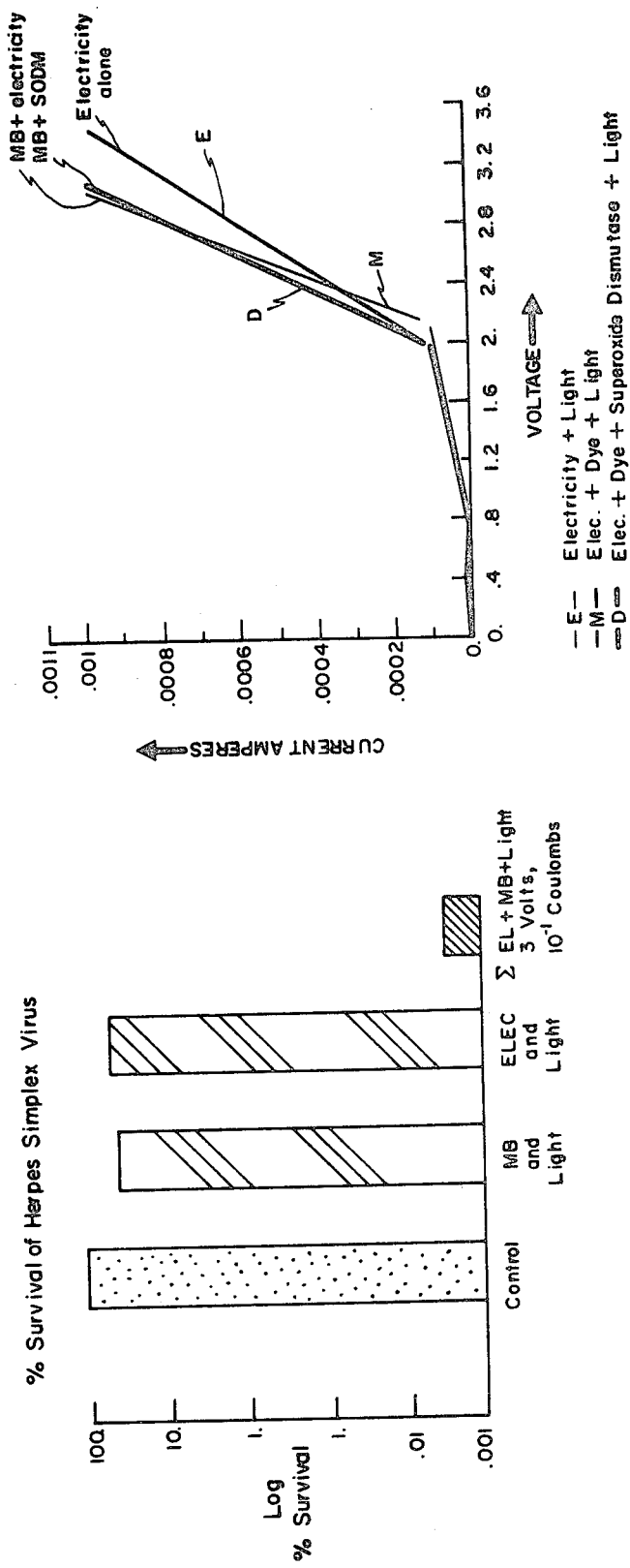

METHOD FOR GENERATING OXYGEN IN AN EXCITED ELECTRONIC STATE AND INACTIVATION OF MICROORGANISMS

This is continuation-in-part of application Ser. No. 879,822, filed Feb. 21, 1978, (now U.S. Pat. No. 4,181,128) which, in turn, is a continuation-in-part of Ser. No. 636,290 (now U.S. Pat. No. 4,139,348), filed Nov. 28, 1975 by the present inventor.

The present invention relates to destruction of Herpes viruses, tumor cell lines, and toxins but it has relevance, as well, to inactivation of other viruses, and to the broader field of production of $O_2^-$, $H_2O_2$, and $OH \cdot$.

In addition to the disclosure in said patent application Ser. No. 636,290, the following journal articles and papers may be used by way of background material and to supplement this specification: "Photodymanic Inactivation of Animal Viruses: A Review" (Wallis et al), *Photochemistry and Photobiology*, 1965, Vol. 4, pp. 159-170; "Oxygen: Boon and Bane" (Fridovich), *American Scientist*, January-February, 1975, Vol. 63, pp. 54-59; "Mechanisms of Photosensitized Oxidation" (Foote), *Science*, Nov. 29, 1968, Vol. 162, No. 3845, pp. 963-969; "Microbe Ingestion and Killing by Neutrophils: Normal Mechanisms and Abnormalities" (Baechner), *Clinics in Haematology*, October, 1975, pp. 609 et seq.; "Electrolytic Univalent Reduction of Oxygen in Aqueous Solution Demonstrated with Superoxide Dismutase" (Forman et al), *Science*, Jan. 12, 1972; "Photosensitized Oxygenation and the Role of Singlet Oxygen" (Foote); "Glow Discharge Polymerization of Tetrafluoroethylene 1, 1 Difluoroethylene, and Chlorotrifluoroethylene" (Rice et al), *Journal of the Electrochemical Society*, September 1976, Vol. 123, No. 9, pp. 1308 et seq; "Cold Plasma Polymerized Films and Their Biological Application" (Mayhan et al), 24th ACEMB, Nov. 4, 1971; "Inactivation of Herpes Simplex Virus with Methylene Blue Plus Electricity" (Swartz et al), Harvard University, July 20, 1977; "Antibody to Genital Herpes Virus: Association with Cervical Atypia and Carcinoma in Situ" (Aurelian et al), *Journal of the National Cancer Institute*, 1970, pp. 455-464.

More than a tenth of the population is plagued by intermittent facial blisters in the oral-facial area, i.e., Herpes simplex virus (HSV-1). Genital Herpes virus (HSV-2) is the next most common presentation of the infection with the virus and is a serious veneral disease. The incidence is 100,000 new primary cases of infection each year in the U.S. In addition, Herpes simplex viruses cause life-threatening disease in compromised individuals and are further implicated and investigated for their cancer-causing (i.e., oncogenic) potential. There is a statistical correlation ($p<0.005$) between anti-HSV-2 antibodies and cervical atypia and carcinoma-in-situ. Such a correlation does not occur with other venereal diseases or in matched controls.

Herpes simplex virus may establish latent infections during the remainder of the host's life. These latent Herpes infections are more widespread than previously believed, as documented by viruses recovered from human trigeminal ganglia in six out of seven randomly selected cadavers. The secondary infections come from latent virus in neuronal and/or lower lying epidermal cells, that is, basal and spickle cell layers. Secondary recurrences are provoked by ultraviolet light, fevers, stress, trauma, menses, corticosteroids, and even acupuncture.

Secondary outbreaks are common with fevers caused by malaria, pneumo- and meningococcus, but are uncommon in staphylococcal, streptococcal, Gram-negative and enteric infections. Synthetic elevation of temperature in humans (to 39.5°-41.5° C.) is followed by orofacial Herpes lesions in thirty to forty-eight hours in nearly half of the subjects.

Herpes simplex virus is a membrane-enveloped DNA virus particle, 150 to 200 nanometers long. The DNA weighs 100 megadaltons, has two loops, and is covered by a 20-sided (i.e., icosahedral) capsid, which is constructed from 162 units (i.e., capsomeres) each composed of six proteins each 25 to 155,000 daltons. The viral proteins are coded in the viral genome but are made within and by the human host cell. The viral DNA and proteins are further covered with an envelope containing lipids, polyamines, and a dozen glycoproteins. This coating is derived from the human host cell on escape. The intact unit is the most common source of infection, although naked Herpes simplex virus DNA is also infectious.

The virus is biochemically categorized into two types. Type 1 or HSV-1 is usually found around the mouth and also causes possibly fatal encephalitis. Type 2 or HSV-2 was historically isolated from the cervix and vagina, or penis. Herpes viruses in primary infections come from infected human hosts. The viral activity of vesicular fluid is roughly $10^5$ viruses (plaque forming units) per millimeter.

Following infection of a cell by Herpes viruses there are two outcomes. The virus either persists non-productively (latently) and/or the cell may become an accomplice to its death, with the escape of viral progeny.

The cycle begins with attachment of a Herpes virus to a specific mammalian cell. The binding is affected by environmental conditions. For example, polyanions such as heparin compete with the virus for attachment at the cell surface and prevent entry of the virus into the cell.

Following attachment, a transmembrane movement of nucleic acid occurs by a fusion of membranes or by pinocytosis, and the virus enters the cytoplasm of the cell. It diffuses to the nucleus to continue its cycle. There, a fraction of the viral DNA is transcribed. The RNA leaves the nucleus to be translated into forty-nine proteins by cytoplasmic ribosomes. Some of those proteins drift back to the mamalian nucleus. One protein—viral specific DNA polymerase—synthesizes further viral DNA within four hours of virus entry into the cell. The viruses are assembled in the nucleus and they are enveloped as they leave the nucleus, covered by the inner lamella of the membrane. Eventually, the cell breaks open, releasing viral progeny. Only 15% of the freshly synthesized viral DNA ends up in virions, the net amplification being ~100 for HSV-1.

A number of proposals for inactivation of Herpes simplex virus and other viruses by others are noted in this and the next paragraph, but treatment of viruses in general and Herpes in particular is a continuing and perplexing problem to the medical profession. Vaccines have been tried. Methylene blue (also MB herein) and light are known to be toxic to living organisms when in the presence of oxygen; methylene blue plus light have also been shown to be effective against Herpes simplex and other viruses, and have been used in vivo with varying success.

Although it has been demonstrated that dyes such as acridines can intercalate between base pairs of DNA, it is likely that the electronic excited states of molecular oxygen are involved in the inactivation of viruses. It has been shown that methylene blue and other photoactive dyes are capable of generating singlet oxygen which can form superoxide anion at an electric cathode, that the reduced form of the dye (i.e., leucomethylene blue) can generate superoxide anion directly, and that the products of superoxide anion, hydrogen peroxide ($H_2O_2$), and especially hydroxyl free radical (OH.), may be the actual cause of damage. Other methods effectively inactivate the Herpes simplex viruses in vitro. These include nucleoside analogs such as cytosine arabinoside or adenosine arabinoside and iododeoxyuridine, inhibitors of the Herpes specific DNA polymerase such as phosphonacetic acid, ether and hypochlorous acid.

Accordingly, it is a principal object of the present invention to provide a system and process for inactivation of Herpes simplex virus.

Another object is to provide a system and process for inactivation of other viruses and bacteria as well.

Still another object is to provide a sterilization system and process for the inactivation of biological cells such as tumor cells, for example.

Another object is to provide a system to inactivate toxins (from Red tide, for example), and breakdown chemicals (e.g., polychlorinated biphenyls).

Another object is to generate a system capable of inducing cell division and spawning.

In the work hereinafter disclosed, it was found that at least part of the biological activity that contributed to the inactivation of the Herpes simplex viruses is due to the existence of the superoxide anion ($O_2^-$) and the hydroxyl radical (OH.) that are formed by the combination of electricity, the electroactive mediator methylene blue, oxygen and light.

Thus, a further object is to provide a system and process for generating singlet oxygen and the superoxide anion ($O_2^-$).

A further object is to provide a system capable of generating hydrogen peroxide ($H_2O_2^-$).

Still another object is to provide a system and process for generating the hydroxyl radical or hydroxyl free radical (OH.).

These and still further objects are addressed hereinafter.

The foregoing objects are achieved in a method of inactivation of microorganisms (e.g., viruses and bacteria) as well as to activation and/or inactivation of tumor cells and macromolecules of a more general nature. The method includes providing a solution containing oxygen and the species to be inactivated or otherwise acted upon to light and introducing to that solution small amounts of a component such as, for example, methylene blue, which component is capable of assuming at least one excited electric state when subjected to light at a particular wavelength. Light at said particular wavelength is directed into the solution to irradiate a substantial portion thereof and an electric field is applied to the same portion. The combination of the light and the electric field in the solution serve to activate the component to at least one excited electronic state and the component, thus activated, reacts with the oxygen to raise the oxygen to an excited electronic state. The oxygen activated in the previously described manner reacts in accordance with the Haber-Weiss reaction to produce the hydroxyl free radical which is the main ingredient in bringing about the inactivation. Light frequency and intensity, electric field intensity, oxygen content of the solution, and the amount of the component in the solution constitute controllable parameters that can be adjusted and maintained at values that render the method operative and selective.

The invention is hereinafter described with reference to the accompanying drawing in which:

FIG. 4 is a graph showing survival of Herpes simplex virus when subjected, in vitro, to a combination of methylene blue, light at 6600 Å, and electricity, the methylene blue being in millimolar concentrations, the electricity being delivered at three volts, one hundred microamperes for three minutes and the light at an intensity of 51 microwatts/cm$^2$;

FIG. 5 shows dose response curves giving Herpes simplex virus survival when simultaneously subjected to methylene blue, light, and electricity, similar to the conditions under which the data in FIG. 4 were obtained, the curves of FIG. 5 being plotted as the logarithm of the percent titer of active virus remaining as a function of the product of time and electric current;

FIG. 6 is a bar graph showing logarithmically the percent survival of Herpes simplex virus under the condition indicated;

FIG. 7 is a graph showing the voltage-current relationships for three solutions used in experiments to obtain data of the type shown in FIGS. 4-6;

Figure 1:
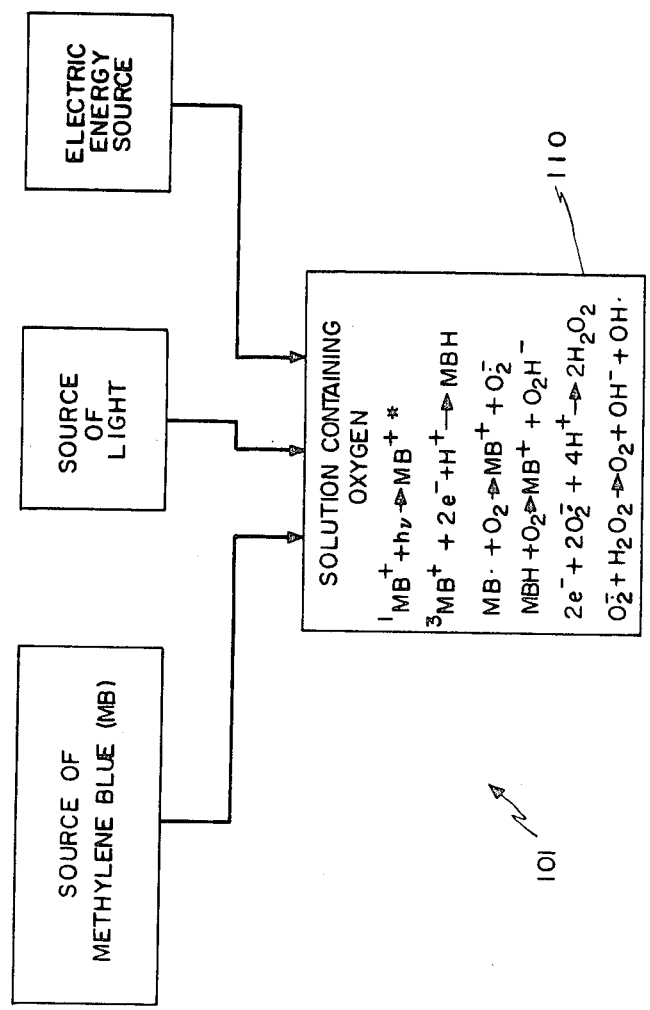
FIG. 1 is a diagrammatic representation of the present invention.

Some preliminary comments are in order. The terms employed herein are used in their regular, accepted sense, but to avoid misunderstanding, there now follows definition of specific terms, others being defined elsewhere in the specification. An important aspect of the invention is that of activating oxygen to its excited electronic and electrically reducible states to provide singlet oxygen $^1O_2$ (the singlet molecular oxygen herein is in the forms ($^1\Delta$) $O_2$ and ($^1\Sigma$) ($O_2$), $O_2^-$ which is the superoxide anion radical, hydrogen peroxide ($H_2O_2$), and OH. which is the hydroxyl free radical. Oxygen in the ground state is a triplet and is designated $^3O_2$ or, more properly ($^3\Sigma$) $O_2$. A number of electroactive mediators can be used to practice the invention, but the one most discussed is methylene blue (also MB herein). Methylene blue in its ground (singlet) state is designated $^1MB^+$, in its excited (singlet) state $^1MB^{+*}$, in its triplet state it is designated $^3MB^+$, and in its excited triplet state it is designated $^3MB^{+*}$. The term MB. refers to the semi-reduced form of methylene blue, and the term MBH refers to leucomethylene blue the 2-electron reduced form of the dye. Several important reactions are given below:

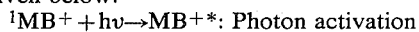
$^1MB^+ + h\nu \rightarrow MB^{+*}$: Photon activation

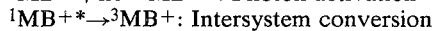
$^1MB^{+*} \rightarrow ^3MB^+$: Intersystem conversion $^3MB^+ + ^3O_2 \rightarrow {}^1MB^+ + {}^1O_2$: Electronic excitation energy exchange $^1O_2 + e^- \rightarrow O_2^-$: Singlet oxygen reduction $^3MB^+ + 1e^- \rightarrow MB.$: MB one electron reduction $^3MB^+ + 2e^- + H^+ \rightarrow MBH$: Methylene blue two electron reduction $MB. + O_2 \rightarrow MB^+ + O_2^-$: Charge transfer $MBH + O_2 \rightarrow MB^+ + O_2H^-$: Charge transfer $2e^- + 2O_2^- + 4H^+ \rightarrow 2H_2O_2$: Dismutation $O_2^- + H_2O_2 \rightarrow O_2 + OH^- + OH.$: Haber Weiss reaction $DNA + OH. \rightarrow DNA$-like fragments Whereas in U.S. Pat. No. 4,139,348 the idea of introducing charge carriers into a species to, for example, reset or affect the chemistry or biology of that species was emphasized, in this application emphasis is placed upon using the combined effects of the activators being described to raise oxygen contained in a solution to an excited electronic state; the oxygen so activated is then used to perform some further function. That further function may be the production of $H_2O_2$ and $OH.$ which, in turn, are applied to, say, Herpes simplex virus to inactivate that virus, the OH. being the active element in such inactivation; or that further function may be the inactivation of a bacteria or toxin or a tumor line or clone such as Burkitts lymphoma; or that further function may be the polymerization of monomers in a synthesizing process. Though the combined effect of methylene blue (MB) or some other electroactive mediator, light and electricity is employed to produce the excited state of oxygen, they enter, to various degrees, into the activity designated "further function" above, as well.

The system herein described, as above indicated, uses a combination of an electroactive mediator or component such as, for example, methylene blue, plus light at certain frequencies and electricity to produce, in a solution 110 in FIG. 1 containing oxygen, the superoxide radical anion ($O_2^-$). In FIG. 1, the system to produce the superoxide radical anion ($O_2^-$) is labeled 101. The production of the superoxide radical anion ($O_2^-$) is in accordance with the chemical reactions above indicated, and from $O_2^-$, hydrogen peroxide and the hydroxyl radical (OH.) are formed. In the discussion that now follows with reference to FIGS. 2 and 3, the inactivation of the Herpes simplex virus HSV-1 is taken up. Compounds of $d^-$ and $f^-$ transition metals, capable of conversion to at least one excited electronic state under the influence of light and an electric field may also be used as electroactive mediators serving to bind with cancer cells. Cisplatinum diamino dichloride exemplifies such compounds.

Figure 2:
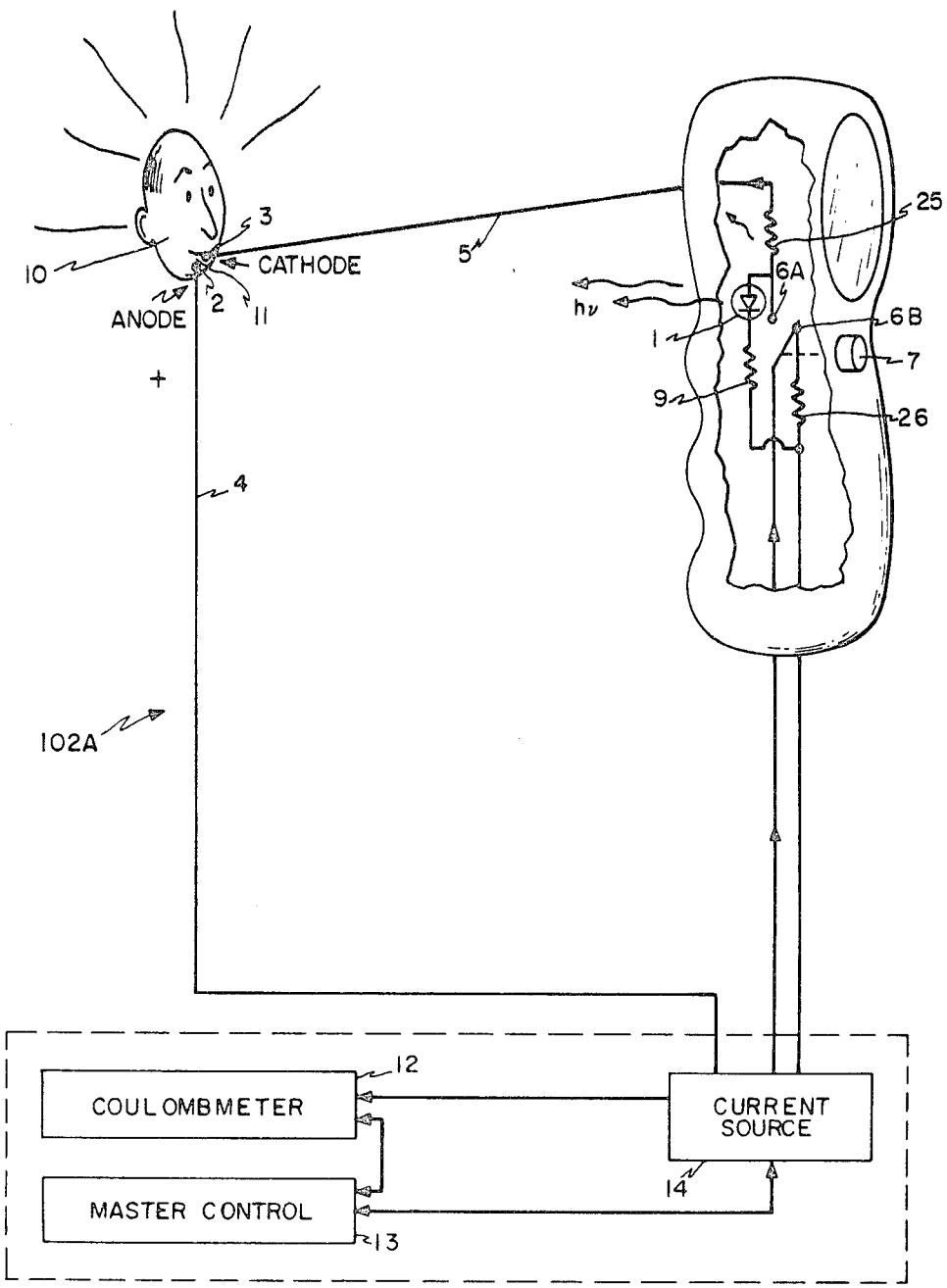
FIG. 2 is a diagrammatic representation of an instrument for inactivating Herpes simplex virus, in vivo and showing the face of a patient being treated.
Figure 3:
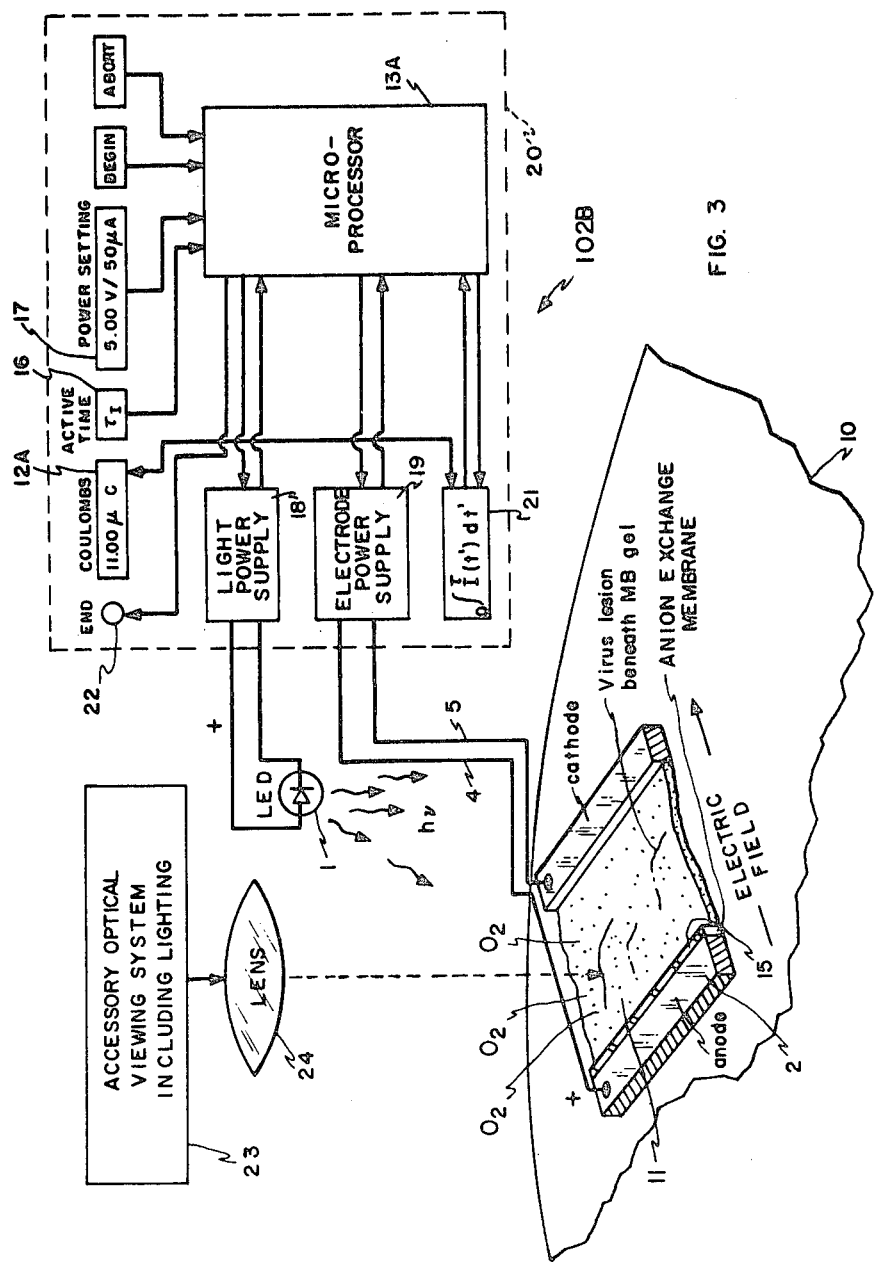
FIG. 3 is a diagrammatic representation of the instrument of FIG. 1 with some elaboration on the controller portion thereof.

In FIGS. 2 and 3 the system shown is applied to a lesion on a patient's face 10, the region of the lesion being labeled 11 in FIGS. 2 and 3. The apparatus for inactivating Herpes simplex virus in the lesion at the region 11 is labeled 102A in FIG. 2 and 102B in FIG. 3, essentially, however, the devices 102A and 102B are the same. Apparent differences are mostly differences in detail or form—not differences in function. In the two figures, identical elements have the same or similar lables; thus, the light emitting diode labeled 1 in FIG. 2 is also labeled 1 in FIG. 3 both figures show an anode 2 and a cathode 3 for purposes discussed in the next paragraph.

The region 11 has applied to it a solution containing methylene blue (MB) which is a component capable of assuming an excited electronic state when subjected to light and an electric field concurrently. A dc voltage (typically ~3 to 5 volts) is applied between conductors 4 and 5, connected respectively to the anode 2 and the cathode 3, to render the anode + with respect to the cathode, to apply an electric field across the region 11. Light (6600Å) is applied simultaneously to the region 11 by the LED 1, the electric field and the light acting cooperatively to activate the MB to leucomethylene blue (MBH). As shown above, the further reactions that occur are the production of $O_2^- \rightarrow H_2O_2 \rightarrow OH.$, and it is mostly the OH. that serves to inactivate the HSV-1 in the region 11, but, even at this juncture, the electricity and light enter the reaction.

Work done indicates that the effect of the electric field occurs in two distinct steps: first there is electromigration of charged molecules to the site of the lesion within the region 11—before this stage useful current flow is quite small—then there is electric current flow through said sites. The device 102A and 102B both have mechanisms to establish predetermined limits on the values of both the voltage and the electric current; such mechanisms are shown in greatest detail in FIG. 3, as later discussed, but first the further elements of FIG. 2 are given.

The system 102A is activated by depressing a button 7 that changes the position of a switch 8 from a contact 6B, where it is in FIG. 2, to a contact 6A. Current flow is across the region 11, through the LED 1, and resistors 25 and 9. The current is provided by an electric current source 14 under the control of a master controller 13; a coulombmeter 12 provides a measure of the amount of charge actually introduced to the region 11. The resistor labeled 26, like the resistors 9 and 25, is a current limiter. The rest of the explanation is made with respect to FIG. 3 wherein the coulombmeter is marked 12A and the master controller is a microprocessor 13A.

The elements within the block designated 20 in FIG. 2 supply the electric energy for the system, the control, and so forth; the LED 1 is external as are the anode 2, the cathode 3 and an anion exchange membrane 15 that serves to achieve charge transfer across the entire lesion. The block 20 includes, in addition to the coulombmeter 12A and the master controller 13A, a timer 16, a power setting circuit 17 (e.g., a zones diode to limit voltage), a light power supply 18, an electrode power supply 19 and an integrator 21. The blocks marked "BEGIN" and "ABORT" are merely buttons to start the inactivation process and abort the process, respectively. A light 22 indicates that the process of inactivation is complete or ended. A necessary optical viewing system 23 is provided, as is a lens 24 permit monitoring of the action in the region 11.

The work done to date using systems equivalent to the system 102B has been done in vitro, and the results shown in FIGS. 4, 5, 6 and 9 are those obtained from in vitro experimentation. There now follows EXAMPLE I, a detailed explanation of the work done with reference to the Herpes simplex viruses, HSV-1 and HSV-2.

EXAMPLE I

Several strains of Herpes simplex viruses 1 and 2 were employed, including the McIntyre strain of HSV-1, strain 333 of HSV-2, strain V3R of HSV-1 (from the American Type Culture Collection) and three clinical isolates obtained from patients with Herpes Labialis and Herpes genitalis. All virus strains were shown to be HSV-1 or HSV-2, by microneutralization techniques. Virus pools were prepared by low multiplicity inoculation ($10^{-2}$ PFU/cell) of confluent cells and then harvesting infected cell cultures at 72–96 hr.

All virus pools had a titer of $4 \times 10^6 - 2 \times 10^7$ plaque forming units per millimeter. Cell lines and virus pools were negative for Mycoplasma growth using Hayflick's media under anerobic conditions.

Methylene blue (MB) was prepared fresh from Sigma or Merck chemical reagent grade stock or from ampoules for IV injection (1%). The dye was kept in the dark until use and the MB was assayed for purity by thin layer chromatography.

Superoxide dismutase (Sigma Chemical, Bovine Blood No. S-8254) was kept frozen until use and then prepared at a calculated activity of 1595 units/ml. The enzyme was added to the electrochemical cell to produce a final concentration of 116 units/ml.

A Mobilite tensor lamp was used on its highest setting and an EEG Radiometer 580-11 was used to generate the output spectrum of the lamp (five centimeter distance between monochrometer and lamp filament). In the experiment the distance was 15 to 25 centimeters. The lamp output was fifty-one $\mu W/cm^2$ between 600–700 nanometers.

Cells were preconstructed from methyl methacrylate and fitted with platinum foil electrodes. The cell dimensions were 3.5 (length)×3.8 (height)×0.8 (width) centimeters and filled with solution (containing HSV) to create a cell constant of 0.017 (length/area). The cells were autoclaved and sealed in aluminum foil.

To carry out the experiments, 1–2 ml of virus pool was transferred to the acrylic curvettes. The cell was immersed in ice water under a Brogard laminar flow hood. Methylene blue (final concentration $10^{--}$–$10^{-7}$) was added and a current source (Keithly 225) applied. Transample voltage (across the electrochemical cell) was followed as a function of time.

At various times during the experiment, representative aliquots were removed by sterile pipette or syringe for plaque assay on Vero cells by the methods described below. Appropriate controls, including virus in the presence of methylene blue alone, or in the presence of electricity alone, were included in every experiment.

Plaquing was done on CV-1 cells in 25 millileter Falcon flasks, using 1% methyl cellulose—2% FBS as an overlay. Flasks with CV-1 cells were trypsinzed and suspended in M100-10% FBS. Cells were grown to confluency in M100-10% FBS (2–3 days) and maintained on M199-2% FBS. Viral logarithmic dilutions were made in M199. The media was poured off and the flasks were inoculated with 0.5 ml of each dilution. Virus adsorbed 1–2 hours with frequent agitation. Five milliliters of a 7% M.C.—2% FBS were overlayed in each flask. The assay was allowed to incubate undisturbed at 3° C. for 5–6 days.

At this time, 2 ml of acetic methesol (1:3=acetic acid methesol) was added for 1 hour to fix the cells. The flasks were washed and the number of plaques counted.

The results of the foregoing experiments are shown in FIGS. 4, 5 and 6. The graph of FIG. 7 shows voltage-current characteristics of the Herpes solutions used above. The curves in FIG. 7 are marked E, M and D to indicate respectively the effects of electricity and light alone; electricity, light and MB; and electricity, MB, light and superoxide dismutase.

The foregoing techniques and the results are summarized, to some extent in this paragraph. The HSV-1 and HSV-2 were inactivated in solutions of methylene blue when electricity was applied for periods from 60–300 seconds (3 volts, $10^{-6}$ to $10^{-1}$ coulombs transferred). The viruses were grown in Vero or Hep2 cells, assayed on CV-1 cells under a methyl cellulose overlay, and typed by a microneutralization method. Virus titers were consistently between $6 \times 10^6$ and $2 \times 10^8$ PFU/ml. When 1 ml of a virus pool was made 1.0 micromolar with methylene blue and a current source applied, a rapid decrease in the plaque forming titer of virus was detected when subsequently assayed on CV-1 cells under methyl cellulose. In 60 seconds with 0.1 microampere current, 99% of Herpes simplex was inactivated. In 120 seconds at 1 milliampere current, 99.97% of input virus was inactivated. In control experiments with methylene blue alone or electricity alone, some inactivation of the virus occurred, but this was significantly less than when the two modalities were combined. Herpes simplex virus inactivation was prevented by the addition of superoxide dismutase to the medium. Since superoxide dismutase is a potent inactivator of superoxide anion, this suggests that the inactivation of Herpes simplex virus is mediated by superoxide free radical formation. Thus, methylene blue and light plus electricity is an effective new sterilization method dependent on superoxide free radical formation.

EXAMPLE II

Solutions of mammalian lymphoblasts and methylene blue were subjected to light and electricity. Controls included samples exposed to light alone, light plus MB, $H_2O_2$ alone, $H_2O_2$ and MB, and electricity alone.

A Keithly current source, voltmeter, and unplatinized platinum electrodes completed the electric system prior to broth (containing MB and lymphoblasts) insertion into the curvettes. Transample leakage impedances (without broth) were greater than 2 megaohms. One milliliter samples were taken at varying times. Electric current magnitude was varied over the course of each experiment.

Total cell counts were followed as a function of time following application of electric current or control chemicals. The cell count was compared to the increasing control cell count (no dye, no electricity, plus light). The viability of lymphoblasts was determined by their ability to bleach Trypan blue.

Figure 9:
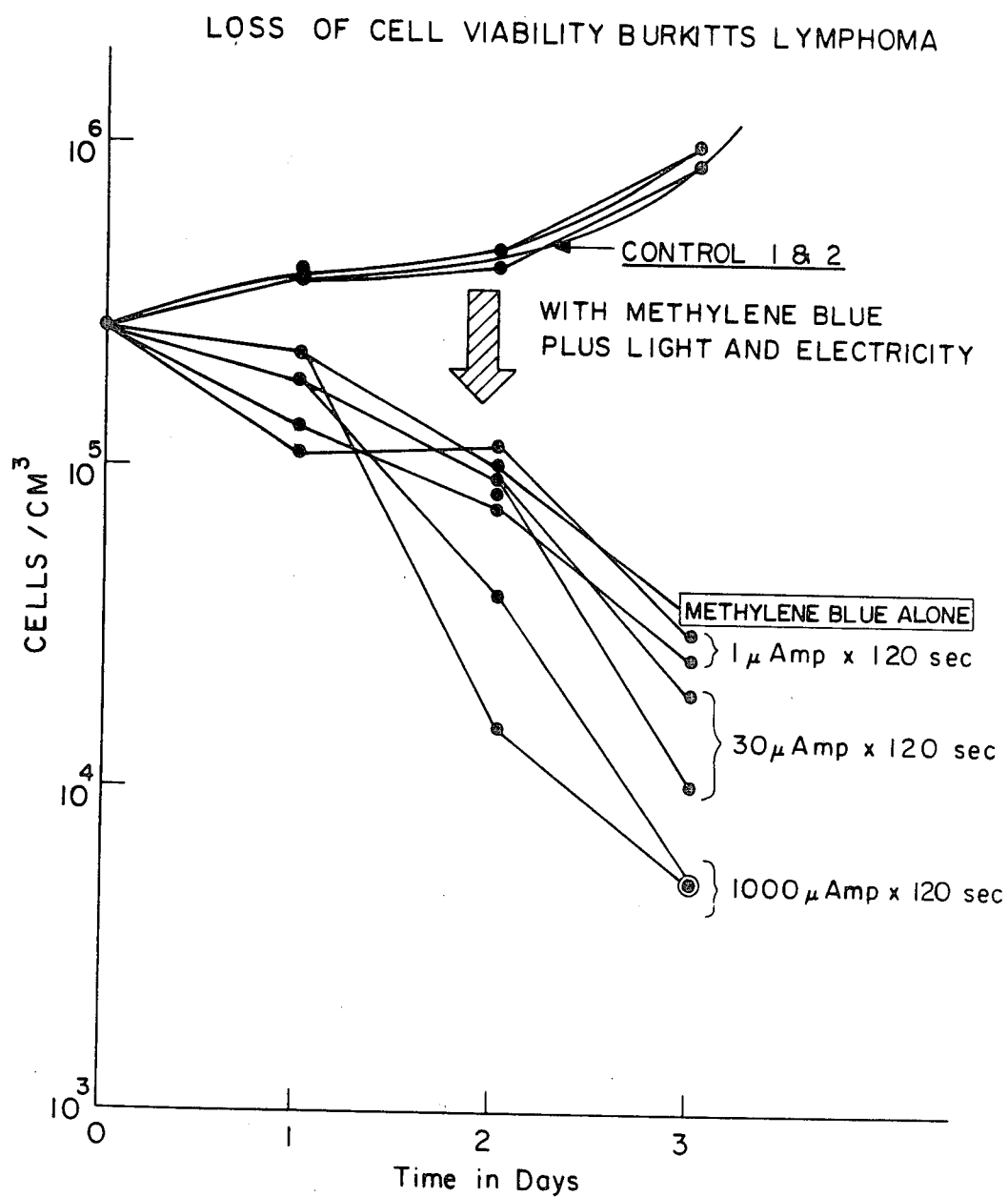
FIG. 9 is a graph showing the combined effect of methylene blue plus light and methylene blue, plus light, plus electricity on Burkitts lymphoma cells.

The results are shown in FIG. 9. The electroactive mediator (active component) may be chemically modified to enhance its binding to a selected cell type or to selected cell types. For example, methylene blue may be covalently bonded to conconavalin A to enhance its binding to mammalian lymphoblasts, e.g. human lymphoblasts. The electroactive mediator thus modified may be used to generate oxygen in an excited electronic state in vivo.

In the explanation given above with reference to FIGS. 2 and 3, the light source indicated is an LED that emits radiation at 6600 Å. For treatment of tumors within patients, such a relatively low intensity light source will not suffice. For internal tumors in breasts and other parts of the body, the MB can be taken internally and the necessary light is applied using stroboscopic techniques. It is proposed, therefore, for present purposes to irradiate a patient with high intensity stroboscopic light from a light source. Toward that end the patient is disposed within an ellipsoid with a reflecting interior, the light source being disposed along a focal line of the ellipsoid of the patient at the other; hence the patient is bathed in high intensity radiation. However, such radiation contains a great deal of infrared radiation which will harm the patient and is not particularly useful for present purposes (frequencies in and around 6600 Å are what is needed). To remove the infrared radiation, the patient is immersed in red-colored water which removes most of the unwanted frequencies, but passes the 6600 Å radiation.

The method described above may be employed, also, to produce vaccines, in vitro. This is accomplished by subjecting viruses, cells, toxins and the like, in vitro, concurrently to light of appropriate frequency and to electricity; but, in this case the reaction is terminated short of complete inactivation.

Figure 8:
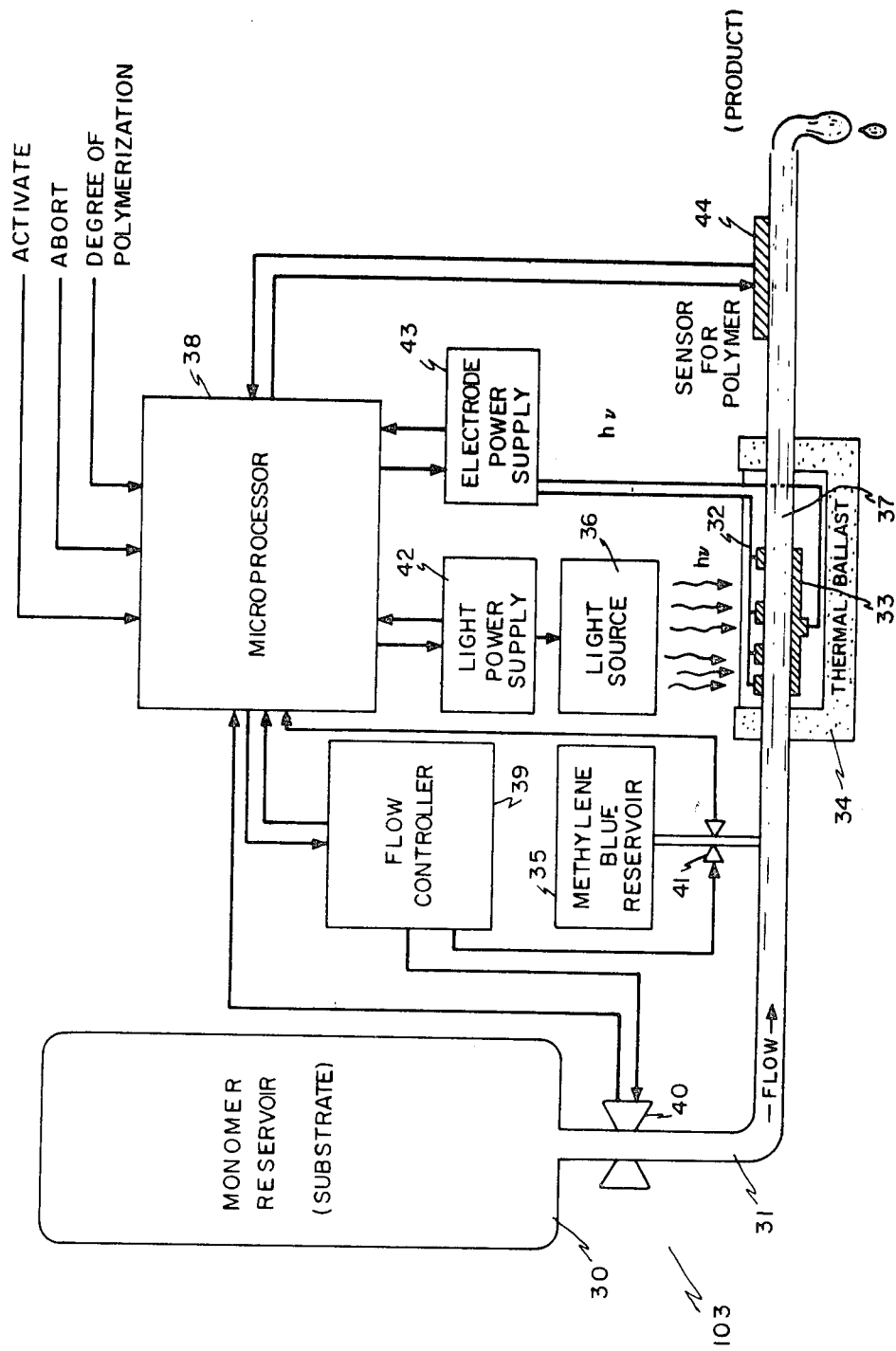
FIG. 8 is a block diagram representation of a continuous polymerizer system.

The system shown at 103 in FIG. 8 serves to polymerize monomers in a polymerization process. The monomer species so polymerized may be, for example, methymethacrylate which, in the presence of $O_2^-$ or OH. forms the polymer. Briefly, a monomer species from a monomer reservoir 30 flows as a solution containing oxygen through a pipe 31 past electrodes 32 and 33 in a thermally insulated chamber 34. Prior to entry there is added to the monomer solution methylene blue from reservoir 35. While the solution containing the monomer and methylene blue is the region labeled 37 between the electrodes 32 and 33, it is subjected to light, as before, from a light source 36, and electricity that flows between electrodes 32 and 33. The combination of MB, light and electricity causes free radicals to form which initiate polymerization.

While the solution is in the region 37 $O_2$ and OH. are formed in the manner explained previously. These free radicals begin the polymerization process (see the Rise et al and Mayhan et al journal articles).

The system 103 further includes a microprocessor 38 to control the various operations of the system, a flow controller 39 to control the flow through valves 40 and 41 for the monomer and MB, respectively, a light power supply 42 and electrode power supply 43. A sensor 44, which may be a dielectric bridge notes the efficiency of the system 103 in converting the monomer to a polymer and provides signals for the microprocessor to effect changes in any one of the MB, light intensity, electric field in the region 37 and/or the rate of flow of the monomer.

There are contained in this paragraph and the next paragraph a few general comments about oxygen, and its importance to our life systems. Molecular oxygen has a great affinity for electrons and, hence, acts as an electron sink during respiration of humans, for example, to power the life systems. Ironically, the intermediaries of oxygen metabolism, $O_2^-$, $H_2O_2$ and, especially, OH., are toxic. So living systems evolved molecules (e.g., hemoglobin) capable of transporting and metabolizing (e.g., cytochromes) molecular oxygen, while detoxifying (e.g., catalases, superoxide dismutases, and β-carotenes) its metabolites.

Molecular oxygen in its ground state is a di-radical with two electrons split between a pair of degenerate anti-bonding orbitals ($\pi^*+$ and $\pi^*-$) which have $\pm h$ angular momentum around the oxygen-oxygen intramolecular bridge. The oxygen atom in the ground state has a single electron in each $\pi^*$ orbital; since these are aligned, this is a triplet state, in fact, the ($^3\Sigma$) state, as noted above. Fortunately, ground state oxygen is non-reactive. It is in its excited electronic states that oxygen performs its functions, as previously indicated herein.

Figure 10:
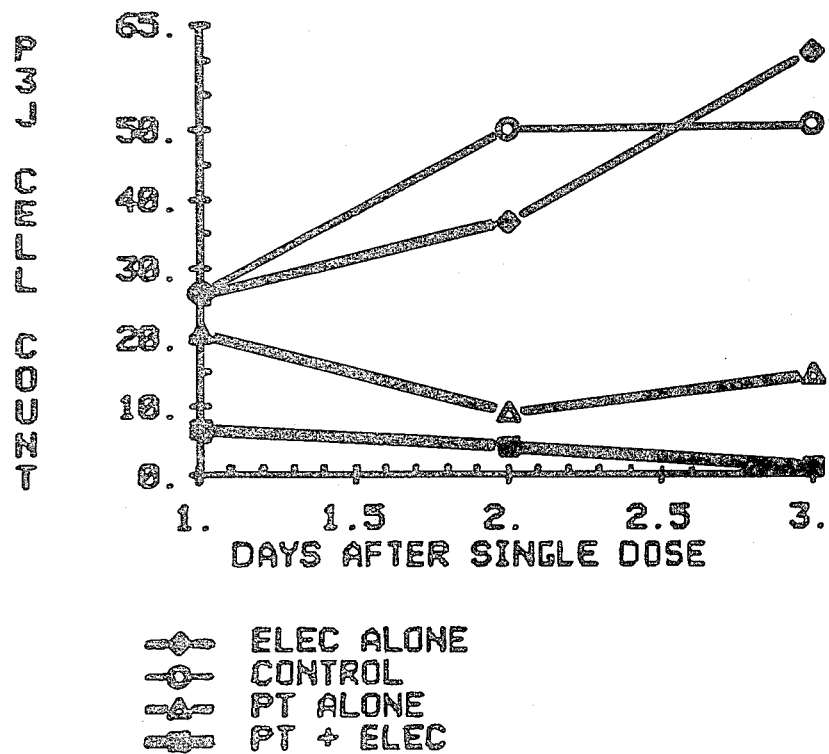
FIG. 10 is a graph showing the combined effect of electricity, light and cis-platinum upon Burkitts lymphoma cells.

In FIG. 10 the cells acted upon are again Burkitt' lymphoma cells as in FIG. 9, but the electroactive mediatior in the work depicted in FIG. 10 is cis-platinum. The results are dramatic; see the lowermost curve in which survival is almost zero three days after a single treatment of combined and concurrent application of light, electricity and cis-platinum. The other curves show survival when electricity (~4 volts) and light alone is applied and cis-platinum and light alone, the further curve being a control.

Further modifications of the invention herein disclosed will occur to persons skilled in the art and all such modifications are deemed to be within the spirit and scope of the invention as defined by the appended claims.

What is claimed is:

1. A method of generating oxygen in an excited electronic state comprising:
    (a) providing covalently bonded methylene blue and conconavalin A;
    (b) adding said covalently bonded methylene blue and conconavalin A to a solution containing oxygen;
    (c) directing light into the solution; and,
    (d) simultaneously applying an electric field to the solution, said light and said electric field serving, in combination, to convert said methylene blue to at least one excited electronic state, the thusly activated methylene blue reacting with the oxygen in the solution to produce oxygen in an excited electronic state.

2. A method in accordance with claim 1 wherein step (b) is conducted by administering said covalently bonded methylene blue and conconavalin A internally to a patient and said oxygen in an excited electronic state is generated in vivo by application of said light and electric field to the patient's body.

3. A method of generating oxygen in an excited electronic state comprising:
    adding a compound of a d− or f− transition metal to a solution containing oxygen, said compound being capable of assuming at least one excited electronic state when the solution is subjected to light and an electric field;
    directing light into the solution; and,
    simultaneously applying an electric field to the solution, said light and said electric field serving in combination to activate said compound to at least one excited electronic state, the thusly activated compound reacting with the oxygen in the solution to produce oxygen in an excited electronic state.

4. The method of claim 3 wherein said compound is cis-platinum diamino dichloride.

* * * * *